United States Patent [19]

Durette

[11] 4,415,731

[45] Nov. 15, 1983

[54] PROCESS FOR THE PREPARATION OF METHYL 2,6-DIDEOXY-α-D-ARABINO-HEXOPYRANOSIDE

[75] Inventor: Philippe L. Durette, New Providence, N.J.

[73] Assignee: Merck & Co., Inc., Rahway, N.J.

[21] Appl. No.: 248,175

[22] Filed: Mar. 30, 1981

[51] Int. Cl.³ .......................... C07H 5/02; C07H 1/00
[52] U.S. Cl. .................................... 536/18.4; 536/18.5
[58] Field of Search .................. 536/4, 122, 4.1, 18.4, 536/18.5

[56] References Cited

U.S. PATENT DOCUMENTS 2,365,776 12/1944 Raymond et al. ...................... 536/4
2,847,413 8/1958 Folkers et al. .......................... 536/4
3,817,978 6/1974 Jenkins et al. ...................... 536/122

OTHER PUBLICATIONS

Durette, "Chem. Abst.", vol. 94, 1981, p. 175, 436(q).
Nashed et al., Abstracts Papers, 181st ACS National Meeting, CARB 25, 1981.

Primary Examiner—Johnnie R. Brown
Attorney, Agent, or Firm—Daniel T. Szura; Hesna J. Pfeiffer

[57] ABSTRACT

Disclosed is a process for preparing methyl 2,6-dideoxy-α-D-arabino-hexopyranoside from methyl 2-deoxy-α-D-glucopyranoside.

2 Claims, No Drawings

PROCESS FOR THE PREPARATION OF METHYL 2,6-DIDEOXY-α-D-ARABINO-HEXOPYRANOSIDE

BACKGROUND OF THE INVENTION

This invention relates to the chiral total synthesis of the known antibiotic (+)-thienamycin (I):

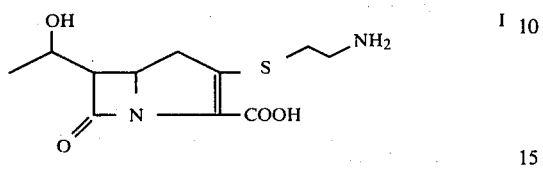

More specifically, this invention relates to a process for preparing methyl 2,6-dideoxy-α-D-arabinohexopyranoside (III) from methyl 2-deoxy-α-D-glucopyranoside (II) by a regioselective halogenation and hydrogenolysis step. The following iodination/hydrogenolysis scheme is preferred and illustrative:

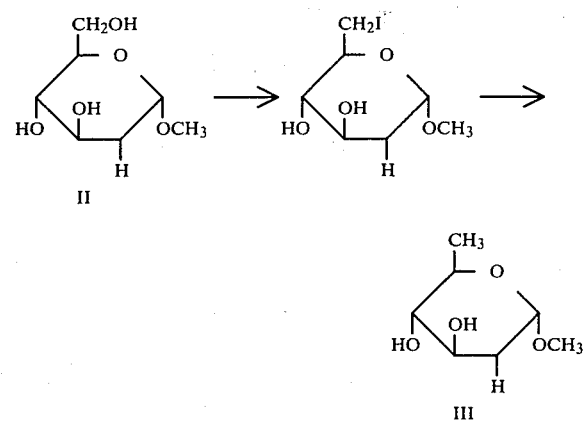

Compound III, methyl 2,6-dideoxy-α-D-arabinohexopyranoside, is useful in the total synthesis of (+)-thienamycin in a manner which is described and claimed in concurrently filed, commonly assigned U.S. Patent applications Ser. Nos. 248,177, now U.S. Pat. No. 4,384,998, 248,116, now U.S. Pat. No. 4,324,900 and 248,174 filed Mar. 30, 1981 of Philippe L. Durette. These co-pending, commonly assigned applications are hereby incorporated by reference to the extent that they disclose the utility for compound III. Also incorporated herein by reference is co-pending commonly assigned U.S. Patent application Ser. No. 112,058 filed Jan. 14, 1980, now abandoned which is directed to a process for the total synthesis of thienamycin, which total synthesis crosses at an intermediate common to said process disclosed in U.S. Ser. No. 248,177 filed Mar. 30, 1981. Also incorporated by reference are U.S. Pat. No. 4,234,596 (issued 11-18-80), and EPO Application No. 79,101,307-1 filed 5-1-79 (publication No. 0007973), which publications disclose schemes of total synthesis which can be fed by common intermediates made available by the presently disclosed and claimed process.

DETAILED DESCRIPTION OF THE INVENTION

The process of the present invention may conveniently be represented by the following reaction diagram:

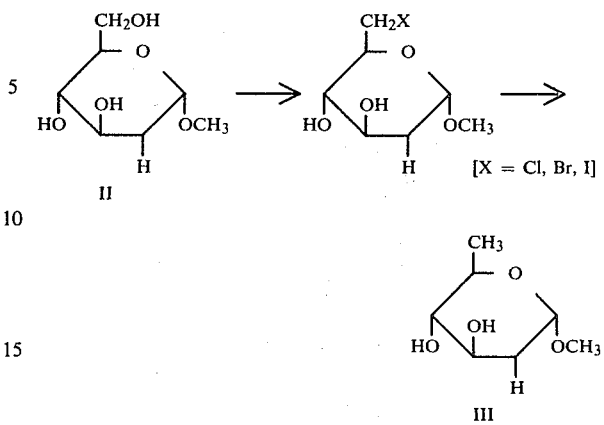

In words relative to the above reaction diagram, desired final product III is obtained via the regioselective halogenation (X=Cl, Br, or I; iodination is preferred) of the primary C-6-hydroxyl of II followed by hydrogenolysis of the resulting intermediate. It should be noted that the starting material methyl 2-deoxy-α-D-glucopyranoside (II) is known, and its preparation from D-glucose (via D-glucal) or 2-deoxy-D-glucose is known; see, for example, I. W. Hughes et al. in *J. Chem. Soc.* 2846 (1949).

In general, starting material II in a solvent such as toluene, benzene, dimethylformamide, dichloromethane or the like is treated with an iodinating agent (or other halogenating agent) such as methyltriphenoxyphosphonium iodide; iodotriphenoxyphosphonium iodide; triphenylphosphine-N-iodosuccinimide; triphenylphosphine-tetraiodomethane; triphenylphosphine-2,4,5-triiodoimidazole; triphenylphosphine, iodine, and imidazole; or the like at a temperature of from 20° to 100° C. for from 1 to 24 hours. The hydrogenolysis to yield desired compound III is typically conducted in a solvent such as methanol, ethanol, ethyl acetate or the like, at a temperature of from 20° to 50° C. in the presence of a catalyst such as Raney nickel, palladium-on-charcoal, palladium black, palladium hydroxide, nickel boride (prepared by the reduction of various nickel salts with sodium or potassium borohydride), or the like; and an acid acceptor (base) to remove hydrogen halide, such as triethylamine, diethylamine, iPr₂NEt, barium carbonate, sodium acetate, or the like; under a hydrogen pressure of from 1 to 5 atmospheres. Typically, the hydrogenolysis procedure may be conducted in the same solvent which yielded the halo intermediate. It has been discovered that the above described transformation II→III is regiospecific. Transformation II→III may also be accomplished by the following scheme:

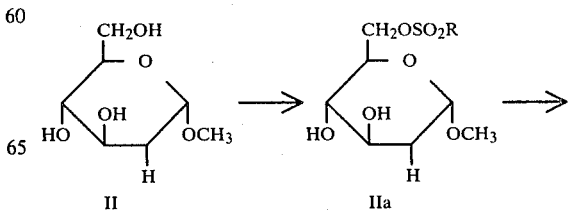

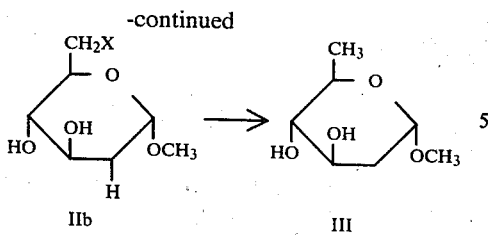

wherein X is halogen as previously defined and R is: alkyl or substituted-alkyl having 1-6 carbon atoms such as methyl, trifluoromethyl, or the like; or phenyl or substituted-phenyl such as p-methylphenyl, p-nitrophenyl, p-bromophenyl, or the like.

The transformation II→IIa is accomplished by treating II in a solvent such as dichloromethane, chloroform, diethyl ether or the like with an alkane- or substituted-alkanesulfonyl chloride, alkane- or substituted-alkanesulfonic anhydride, a phenyl- or substituted-phenylsulfonyl chloride, or a phenyl- or substituted-phenylsulfonic anhydride, or the like, in the presence of a base such as triethylamine, iPr$_2$Net, pyridine, 4-dimethylaminopyridine, or the like at a temperature of from $-76°$ to 50° C. for from 20 minutes to 7 days.

The transformation IIa→IIb is accomplished by treating IIa in a solvent such as acetonitrile, dimethylformamide, dimethylsulfoxide, or hexamethylphosphoramide with an alkali halide, such as lithium bromide, sodium bromide, sodium iodide, or the like, or a tetraalkylammonium halide, such as tetraethylammonium chloride, tetra-n-butylammonium bromide, tetra-n-butylammonium iodide, or the like, for from 0.5 to 24 hours at 20° to 150° C.

The transformation IIb→III is as described previously.

Finally, it should be noted that the transformations IIa→III or IIb→III can also be accomplished with nucleophilic metal hydride reagents, such as lithium aluminum hydride, sodium borohydride, lithium triethylborohydride, or the like, or with trialkyltin hydrides (free radical mechanism) such as tri-n-butyltin hydride, or the like.

In the foregoing word description of the above schematic reaction diagram, for the transformation II→III, it is to be understood that there is considerable latitude in selection of the precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps given is more in the nature of a descriptive convenience than a necessary requirement; for one will recognize that the mechanically dissected scheme represents a unified scheme of synthesis and that certain steps, in actual practice, are capable of being merged, and conducted in a near simultaneous order as indicated.

The following examples recite a precise scheme of synthesis. It is to be understood that the purpose of this recitation is to further illustrate the total synthesis and not to impose any limitation. All temperatures are in °C.

EXAMPLE 1

Preparation of Methyl 2,6-Dideoxy-α-D-Arabino-Hexopyranoside

Step A Methyl 2,6-dideoxy-6-iodo-α-D-arabino-hexopyranoside

A mixture of crude methyl 2-deoxy-α-D-glucopyranoside [prepared by the process set forth in I. W. Huges, W. G. Overend, and M. Stacey, J. Chem. Soc., 2846 (1949)] (12.0 g, 67.4 mmol), imidazole (13.76 g, 202 mmol), iodine (23.92 g, 94.2 mmol), and triphenylphosphine (26.50 g, 101 mmol) in toluene (900 mL) is stirred for 5 hours at 75° C., cooled, and filtered through Celite. The gummy residue in the reaction vessel is triturated with chloroform and the resulting solid filtered. The combined filtrates are evaporated under vacuum, and the syrup is subjected to preparative high-performance-liquidi-chromatography on silica gel (Prep-PAK TM 500 silica columns using a Waters Associates Prep LC/System 500 (2:1 chloroform-ethyl acetate) to give the desired product as a colorless syrup; yield 14.8 g (76%); $[α]_D +97°$ (c 0.9, chloroform); $^1$H NMR (300 MHz, D$_2$O):δ1.76 (m, H-2ax, JH-1, H-2ax=3.7 Hz, J H-2ax, H-2eq=13.4 Hz, J H-2ax, H-3=11.8 Hz); 2.18 (broad dd, H-2eq, J H-2eq, H-3=5.0 Hz); 3.43 (s, OCH$_3$); 3.91 (oct, H-5); 4.92 ppm (broad d, H-1).

Anal. Calcd for C$_7$H$_{13}$IO$_4$ (288.1) C, 29.18; H, 4.55; I, 44.05 Found: C, 29.12; H, 4.72; I, 43.88.

STEP B

A mixture of methyl 2,6-dideoxy-6-iodo-α-D-arabino-hexopyranoside (11.34 g, 39.4 mmol), triethylamine (3.6 ml), and Raney nickel (~18 g) in methanol (250 ml) is hydrogenated at a pressure of 2.7 atm for 48 hrs. at room temperature. The catalyst is then removed by filtration through Celite, and the filtrate is evaporated under vacuum. The resulting syrup is dissolved in a small volume of methanol (~10 ml), and the solution is passed through a short column of AG501-X8 mixed bed resin to remove triethylamine hydroiodide. The effluent is evaporated under vacuum, and the syrup is dissolved in a small volume of chloroform (~10 ml), and the solution is chromatographed on silica gel (Merck No. 7734) (25:1 chloroform-methanol) to remove nickel salts. The pure product is obtained as a chromatographically homogeneous colorless syrup; yield 6.42 g (99%); $^1$H NMR (300 MHz, D$_2$O):δ1.29 (d,C-CH$_3$); 1.74 (m, H-2ax, J H-1, H-2ax=3.6 Hz, J H-2ax, H-2eq=13.5 Hz); 2.16 (broad dd, H-2eq, J H-2eq, H-3=5.0 Hz); 3.13 (t, H-4, J H-3, H-4=J H-4, H-5=9.5 Hz); 3.36 (s, OCH$_3$); 3.72 (m, H-5); 3.85 (m, H-3); 4.87 ppm (broad d, H-1).

Anal. Calcd for C$_7$H$_{14}$O$_4$ (162.2): C, 51.84; H, 8.70 Found: C, 51.55; H, 8.63.

What is claimed is:

1. A process for preparing methyl 2,6-dideoxy-α-D-arabino-hexopyranoside of the structure:

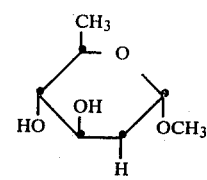

comprising the steps of:

iodinating with an iodinating agent selected from: methyltriphenoxyphosphonium iodide; iodotriphenoxyphosphonium iodide, triphenylphosphine-N-iodo-succinimide; triphenylphosphine-tetraiodomethane; triphenylphosphine-2,4,5-triiodoimidazole; triphenylphosphine, iodine, and imidazole the substrate methyl 2-deoxy-α-D-glucopyranoside wherein hydroxyl groups are unprotected to yield:

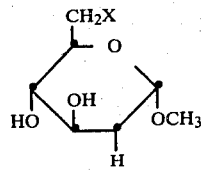

followed by catalytic hydrogenolysis; wherein X is iodo.

2. The compound:

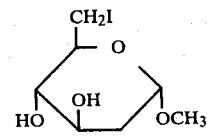

* * * * *